United States Patent [19]

Herring

[11] Patent Number: 4,675,385

[45] Date of Patent: Jun. 23, 1987

[54] ISOLATION OF HUMAN PLASMA PROCOAGULANT PROTEIN FACTOR VIII FROM BIOLOGICAL FACTORS

[75] Inventor: Steven W. Herring, San Dimas, Calif.

[73] Assignee: Alpha Therapeutic Corporation, Los Angeles, Calif.

[21] Appl. No.: 716,456

[22] Filed: Mar. 27, 1985

[51] Int. Cl.[4] .................... A61K 35/14; A61K 35/16; C07K 3/20
[52] U.S. Cl. .................................. 530/383; 530/413; 530/830
[58] Field of Search ...................... 260/112 B, 112 R; 530/383, 413, 830; 514/21

[56] References Cited

U.S. PATENT DOCUMENTS

| | | | |
|---|---|---|---|
| 3,637,489 | 1/1972 | Haller | 210/31 C |
| 3,657,116 | 4/1972 | Haller | 210/31 C |
| 3,920,625 | 11/1975 | Anderson et al. | 260/112 B |
| 4,069,216 | 1/1978 | Shanbrom | 260/112 B |
| 4,108,603 | 8/1978 | Regnier et al. | 23/230 B |
| 4,348,315 | 9/1982 | Birger et al. | 260/112 B |
| 4,377,482 | 3/1983 | Rivier | 260/112 R X |
| 4,397,841 | 8/1983 | Johnson | 260/112 B |
| 4,503,035 | 3/1985 | Pestka et al. | 424/85 |

OTHER PUBLICATIONS

Paper by Phillip J. Fay et al., "Purification and Characterization of a Highly Purified Human Factor VIII Consisting of a Single Type of Polypeptide Chain", Proc. Natl Acad. Sci., vol. 79, pp. 7200–7204, Dec. 1982.
Bio-Rad Price List J., Jan. 1984 and earlier, pp. 94–99, 88–89 and 5.
T. W. Hearn et al., "HPLC Peptides and Protein", American Laboratory, vol. 14(10), Oct. 1982, pp. 1 et seq.
Abstracts of 4th International Symposium on HPLC of Proteins, Peptides, and Polynucleotides, Dec. 10th–12th, 1984, Baltimore, MD.
Paper Titled "Isolation of Human Factor VIII:C by Preparative High Performance Liquid Chromatography", Dec. 10, 1984.
Paper by T. Hashimoto et al., "High Speed Aqueous Gel-Permeation Chromatography", Journal of Polymer Science: Polymer Physics Ed., vol. 16, 1789–1800 (1978).

*Primary Examiner*—Howard E. Schain
*Attorney, Agent, or Firm*—Christie, Parker & Hale

[57] ABSTRACT

A rapid and simple process for purifying human, bovine and porcine procoagulant protein Factor VIII on a large scale using sequential high performance size exclusion chromatography under, first, low salt concentration conditions and, second, under high salt concentration conditions from reconstituted commercial Factor VIII:C (complexed Factor VIII) concentrate. The chromatographic separation is carried out on a high performance size exclusion chromatographic column packed with porous beads having a particle size of from about 13 to about 35 microns, pore diameters of from about 500 to about 2000 Angstroms and a pore volume of from about 1.0 to about 1.8 ml per gram. The first chromatographic separation is carried in a buffered aqueous solution using the buffered aqueous solution as an eluant. The low molecular weight constituents (impurities) are separated from Factor VIII and the high molecular weight constituents (impurities). A second chromatographic separation may be carried out after Factor VIII has been dissociated in a buffered solution having a concentration of from about 0.25 to about 0.45M calcium ion. The second chromatographic column is packed with some packing as the first column and is eluted with a buffered aqueous solution containing 0.25 to 0.45M calcium ion. In a column of 2.5×60 cm, 4 gms of commercial Factor VIII concentrate can be purified in less than two hours. The process is amenable to scale up.

25 Claims, 3 Drawing Figures

Fig. 2

ISOLATION OF HUMAN PLASMA PROCOAGULANT PROTEIN FACTOR VIII FROM BIOLOGICAL FACTORS

BACKGROUND OF THE INVENTION

This invention relates to a method of purifying human plasma procoagulant protein Factor VIII:C from Factor VIII concentrates.

For several decades there has been considerable interest in the human plasma Factor VIII procoagulant protein because of its value in the treatment of hemophilia A. Invivo or circulating Factor VIII is known to be a large complex composed of two different proteins, a carrier protein (von Willibrand factor) and the procoagulant protein Factor VIII:C which are linked together by noncoavalent bonds. Von Willibrand factor interacts with platelets in a way that promotes primary hemostasis and is usually designated Factor VIII R (ristocetin cofactor or von Willebrand antigen). Hemophilia A patients, that is those patients suffering from classical hemophilia, lack functional Factor VIII:C and require infusion of Factor VIII:C in order to overcome bleeding episodes.

Factor VIII (also known as the Antihemophilic Factor A or AHF) is commercially available as a lyophilized sterile dry powder which is reconstituted with sterile distilled water or sterile physiological saline for infusion into a hemophilia A patient.

A number of processes exist for the preparation of plasma concentrates for clinical use which contain the Factor VIII complex or parts thereof together with other plasma constituents. The concentrates have been a boon to hemophiliac A patients; unfortunately, the specific activity of the concentrates is low and therefore great volumes of constitute solution must be injected into the patient for treatment of hemophilia A. A number of methods have been developed for preparing concentrates with higher specific activities; unfortunately, most of these methods have very low recovery rates and are costly. Because of the low recovery rates and high cost of the methods, these methods have not been utilized on a commercial scale to produce Factor VIII concentrates having a high activity.

U.S. Pat. No. 3,920,625 to L. O. Andersson et al discloses a 12 step process for isolating Factor VIII (AHF) and the B-Factor from blood plasma. An essential step according to the inventors is the adsorption of at least one of these factors, in a liquid system onto a water-soluble gel matrix thus leaving the other factor in the supernatant liquid.

U.S. Pat. No. 4,069,216 to E. Shanbrom discloses a method of selectively removing the fibrinogen from a solution of blood plasma or plasma by treating the buffered plasma with polyol and maintaining the resulting mixture at a temperature of from about 0° C. to about 5° C. until precipitation of the fibrinogen occurs.

U.S. Pat. No. 4,397,841 to J. H. Johnson is directed to a method of concentrating Factor VIII by fractionating plasma with a sequence of adsorption steps employing two different water-insoluble cross-linked polyelectrolyte copolymers, each in the presence of exogenous heparin. In the first adsorption step, Factor IX complex is removed from the supernatant liquid. In the second adsorption step, Factor VIII is adsorbed and recovered from the adsorbent after separation of the adsorbent from the supernatant liquid. Recoveries of 40-70% of the original Factor VIII are reported.

U.S. Pat. No. 4,348,315 to E. G. Birger Blomback et al discloses a process for the purification and/or concentration of Factor VIII complex by dissolving the Factor VIII complex, including impurities, in a solution containing at least 1.5M glycine, having a pH of about 6.3-7.8 and maintaining the resulting mixture at a temperature of from 15° C. to 40° C. to precipitate out impurities leaving the Factor VIII in the supernatant liquid.

U.S. Pat. No. 3,637,489 to W. Haller is directed to a process for the separation of blood components using steric chromatography. Haller discloses that it is known to separate serum proteins with the aid of gel filtration, also called gel chromatography, steric chromatography, exclusion chromatography or gel permeation chromatography. This method utilizes porous auxilliary substances which have pores of such dimensions that molecules to be separated diffuse into and out of the pores at different velocities or are prohibited from entering the pores. Haller further discloses they can be used to fractionate serum proteins on a laboratory research scale but cannot be used for large-scale fractionation and particularly if the product should qualify for medical applications.

U.S. Pat. No. 3,657,116 to W. Haller discloses a process for the separation of blood components by fractionating the blood plasma or serum in a chromatographic column filled with porous glass particles.

U.S. Pat. No. 4,108,603 to F. E. Regnier et al discloses a method of analysis of hemoglobin variance by high speed liquid chromatography at high pressures employing a bonded phase inorganic support column. The bonded phase support preferably includes ion-exchange groups bonded through a carbohydrate intermediate to controlled porosity glass.

The paper by Phillip J. Fay et al, "Purification and Characterization of a Highly Purified Human Factor VIII Consisting of a single Type of Polypeptide Chain", Proc. Natl. Acad. Sci., Vol. 79, pages 7200-7204, December, 1982 discloses a procedure for purification of human Factor VIII from plasma which utilizes calcium dissociation and differential size and charge chromatography. The human Factor VIII was purified over 350,000 fold (relative to plasma) from a commercial Factor VIII concentrate with a final yield of 13%. The process involves seven steps: a proprietary cryoprecipitation, a column fractionation on a Bio Gel A-15 M column, a ammonium sulfate dialysis, a calcium ion dissociation, a further chromatographic fractionation on a Sepharose (CL-4B column, dialysis and a final chromatographic separation on a QAE cellulose column.

Bio-rad Price List J, January 1984, pages 94-99, discloses that Bio-Gel TSK columns are suited to separating polycations or neutral polymers, such as polyacrymide (PAM), polyethylene oxide, polyvinyl alcohol (PVA) and the like. Bio-Gel TSK columns are packed with a hydroxylated polyether-based material.

T. W. Hearn et al, "HPLC Peptides and Protein", American Laboratory, Vol. 14(10), October, 1982, page 1 et seq. describes the use of high performance liquid chromatography in peptide and protein separation.

SUMMARY OF THE INVENTION

This inventioon provides a relatively simple process for the rapid isolation of human Factor VIII procoagulant protein from a plasma preparation comprising Factor VIII and impurities designated as high molecular weight constituents and low molecular weight constituents by high performance size exclusion chromatography. The inventive process comprises the steps of
(a) preparing a buffered aqueous composition of the plasma preparation;
(b) separating the low molecular weight constituents from the buffered aqueous composition by introducing the composition on a high speed chromatographic column (HPLC column) of porous, mechanically rigid beads having a particle size of from about 13 to about 35 microns, the particles having pores with diameters of from about 500-2000 Angstroms and a pore volume of from about 1.0 to about 1.8 ml per gram, eluting the column with an aqueous eluant, and selecting and collecting those fractions of the eluant immerging from the column containing Factor VIII and high molecular weight constituents substantially free of the low molecular weight constituents to obtain a second aqueous composition.

The second aqueous composition will contain Factor VIII of enhanced purity. The purity of Factor VIII can be enhance 100 fold, although normally the purity enhancement will be about 20 fold. The specific activity for blood coagulation of Factor VIII and Factor VIII:C in units per milligram of protein is the measure of purity. A wide range of specific activities have been observed for different eluted Factor VIII and Factor VIII:C preparations. It is believed that the specific activity differences between preparations of Factor VIII and Factor VIII:C result from the proteolytic activity of the proteases in the impurities, that is, the low molecular weight constitutes and high molecular weight constituents. The impurities contain proteases that attack Factor VIII and Factor VIII:C and render them inactive for procoagulation. The impurities in each sample of Factor VIII and Factor VIII:C have a different level of proteolytic activity. Thus different preparations of Factor VIII and Factor VIII:C purified in accordance with the present process may have a different ratio of pre-purification specific activity to post-purification specific activity due to the different degrees of proteolytic attack on Factor VIII and Factor VIII:C by the proteases in the impurities.

To minimize proteolytic attack of Factor VIII by the proteases in the impurities, the purification is carried out as quickly as possible. The plasma preparation containing Factor VIII is frozen, or maintained at a low temperature, or maintained in a lyophobic state to minimize protease activity until preparation of the buffered aqueous solution. However even these precautions do not eliminate, entirely, proteolytic attack by the proteases during the chromatographic separations and concentration of the collected fractions.

Factor VIII can be further purified to remove the high molecular weight constituents (impurities) by dissociating Factor VIII to its lower molecular weight form, Factor VIII:C, and separating Factor VIII:C from the high molecular weight constituents (impurities) by high performance size exclusion chromatography. The process comprises the steps of:
(a) dissociating Factor VIII into its lower molecular weight form (Factor VIII:C) in a buffered aqueous composition by adjusting the soluble salt concentration of said composition to at least 0.2M to produce a second aqueous composition; and
(b) separating the higher molecular weight constituents from the second aqueous composition by introducing the composition on a high speed chromatographic column of porous, mechanically rigid beads having a particle size from about 13 to about 35 microns, the particles having pores with diameters of about 500 to about 2000 angstroms and a pore volume of from about 1.0 to about 1.8 ml per gram, eluting the column with an aqueous eluant, and selecting the fractions of eluant immerging from the column containing Factor VIII:C substantially free of the high molecular weight constituents.

The second aqueous composition of the first chromatographic separation or purification, that is the collected fractions containing Factor VIII and high molecular weight constituents substantially free of low molecular weight constituents, can be treated to the second purification step to remove the high molecular weight constituents. The second aqueous composition of the first chromatographic purification can be directly subject to the second purification step as described above. Preferably, the second aqueous composition is concentrated prior to further purification. The concentration can be carried by conventional means known to the art, such as dialysis, lyophilization, evaporation, and the like, preferably by dialysis to prevent concentration of buffering agents and salts.

Most commercial preparations of Factor VIII are prepared from human plasma by proprietary processes such as cryoprecipitation, to produce a freeze-dried or lyophilized Factor VIII powder which has a specific activity of about 1 unit per mg of powder. Although the specific activity of a pure Factor VIII is not known, it is believed that the specific activity is in excess of 5000 units per mg of pure human Factor VIII. Commercial preparations of Factor VIII concentrate contain high molecular weight constituents (impurities) and lower molecular weight constituent (impurities). The nature of these impurities is not fully known, however, they include fibrinogen, von Willebrand protein, carrier protein, other blood coagulation factors and proteases. The present process takes advantage of the molecular weight differences between Factor VIII and the lower molecular weight constituents and between dissociated Factor VIII, Factor VIII:C, and the high molecular weight constituents.

The molecular weight of Factor VIII has been reported from 1,000,000 to 20,000,000. factor VIII can be dissociated in a high salt concentration solution, such as in a 0.3M $CaCl_2$ solution, to its lower molecular weight form, Factor VIII:C. The molecular weight of Factor VIII:C is reported to be from about $0.9 \times 10^5$ to about $3.0 \times 10^5$. (See Fay et al supra).

In the first purification process, the lower molecular weight constituents (impurities) having long deminsions of about 100 nM or less (roughly equivalent to proteinaceous materials having molecular weights of about 1,000,000 or less) are separated from the high molecular weight constituents and the Factor VIII in its high molecular weight form. In the second purification process, Factor VIII is dissociated in a high salt environment to its lower molecular weight forms and separated from the higher molecular weight constituents (impurities) having long dimensions of about 100 nM or more (roughly equivalent to proteinaceous materials having molecular weights of about 1,000,000 or more) by a second chromatographic separation. The process of the present invention permits a 100 fold or more increase in purification of Factor VIII.

It is believed that Factor VIII:C, dissociated Factor VIII, will reassociate in the presence of von Willebrand factor upon removal from a high salt concentration environment. The high salt concentration can be reduced by the addition of water, buffered or unbuffered, or preferably by dialysis.

The impurities associated with Factor VIII comprise proteins, carbohydrates and lipids and complexes thereof. When these constituents have the long distances of the high molecular weight constituents or the low molecular weight constituents they are separated from Factor VIII by the present process. If the Factor VIII is contaminated with bacteria, fungi, virus and/or their components having the long distances of the high molecular weight constituents (impurities), such contaminates with the high molecular weight are separated by the second process from Factor VIII:C.

DETAILED DESCRIPTION OF THE INVENTION

The invention disclosed and claimed herein is for a process for isolating Factor VIII procoagulant protein (Factor VIII) from a plasma preparation comprising Factor VIII, high molecular weight constituents (impurities) and low performance size exclusion chromatography comprising the steps of:

(a) preparing a buffered aqueous composition of a plasma preparation comprising Factor VIII, high molecular weight constituents, and low molecular weight constituents, said composition having a soluble, physiologically compatible inorganic chloride salt concentration of from about 0.07 to about 0.3M and a pH of from about 5.55 to about 8.0;

(b) separating the low molecular weight constituents from said buffered aqueous composition by introducing said composition on a chromagraphic column of porous high performance liquid chromatograph beads having a particle size of from about 13 to about 35 microns, the particles having pores with mean diameters of from about 500 to about 2,000 Angstroms and a pore volume of from about 1.0 to about 1.8 ml/bm, eluting the chromatographic column with a buffered aqueous eluant having a soluble, physiologically compatible inorganic chloride salt concentration of about 0.07 to about 0.3M and a pH of from about 5.5 to about 8.0, and selecting and collecting those fractions of the eluant immerging from the column containing the Factor VIII and high molecular weight constituents substantially free of the low molecular weight constituents to obtain a second aqueous composition.

If desired, the Factor VIII composition of the above purification stage can be separated from the high molecular weight constituents by a process comprising the steps of:

(a) concentrating said second aqueous composition to obtain a third aqueous composition containing Factor VIII and high molecular weight constituents, said third aqueous composition having a protein concentration up to the solubility limits of Factor VIII and the high molecular weight constituents in the third aqueous composition, preferably from about 0.1 to about 200 g of protein per liter of composition;

(b) dissociating the Factor VIII in said third aqueous composition into its lower molecular weight forms by adding a soluble, physiologically, compatible salt to of said third aqueous composition to adjust the salt cation concentration to about 0.2M or more to produce a fourth aqueous composition; and (e) separating the high molecular weight constituents having a molecular weight at least equal to the molecular weight of Factor III from said fourth aqueous composition by introducing said composition on a chromatographic column of porous high performance liquid chromatography beads having a particle size of from about 13 to about 25 microns, the particles having pores with mean diameters of from about 500 to about 2000 Angstroms and a pore volume of from about 1.0 to about 1.8 ml per gram, eluting the chromatographic column with a buffered aqueous eluant having a soluble, physiologically compatible inorganic chloride salt concentration of from about 0.07 to about 0.3M, a soluble, physiologically compatible salt cation concentration above about 0.2 and a pH of from about 5.5 to about 8.0, and selecting the fractions of the eluant immerging from the column containing dissociated Factor VIII:C substantially free of said high molecular weight constituents.

The plasma preparation can be human, bovine or porcine plasma, prefractionated human, bovine or porcine plasma, human, bovine or porcine serum or prefractionated human, bovine or procine serum. Preferably, the plasma preparation is a Factor VIII concentrate, especially a dry hyophilized Factor VIII powder. If a commercial Factor VIII concentrate is employed in the process, it is reconstituted with sterile distilled water or a sterile buffered solution and used in the preparation of the buffered aqueous composition. The buffer used in the buffered aqueous composition can be any of the conventional biochemical buffers, especially buffers with a maximum buffering capacity at a pH between 5.5 and 8.0. The preferred buffer is, imidazole HCl. The soluble, physiologically compatible inorganic chloride salt can be any conventional biochemical chloride salt that does not interact with or denature proteins, such as sodium chloride, potassium chloride, lithium chloride, calcium chloride and magnesium chloride. Preferably, sodium chloride is the soluble, physiologically compatible inorganic chloride salt employed. The ionic concentration of the chloride salt in the composition is maintained at less than 0.5M, preferably between about 0.07 and about 0.3M, and most especially preferred at about 0.15M.

The chromatographic columns are subject to great pressures in high performance liquid chromatography and, accordingly, are constructed out of strong inert metals, such as a stainless steel. The column packings are prepared from materials that are inert to the aqueous solutions used in the chromatographic separation, non-deleterious to and non-reactive with protein, such as Factor VIII and Factor VIII:C, and mechanically rigid so that they undergo little, if any, deformation when subject to the pressure of high performance liquid chromatography. Hydroxylated polyether-based packings, such as Bio-Rad Bio-Gel TSK packing or beads (Toyo Soda Manufacturing Co., Japan) have been found to be suitable. The TSK beads have been reported to be hydrophilic polymer gel containing the group, —$CH_2$-$CHOHCH_2O$—, as the main constituent component (Hashimoto, T., et al; J. Polym. Sci. Polym. Phys. Ed., Vol. 16 (1978), 1789-1800). The particle size of the packing material is critical and must be from about 13 to about 35 microns in order to provide proper interstitial distances between particles through which the large proteins and other impurities may pass. The pores of the porous particles have mean diameters of from about 500 to about 2000 Angstroms, preferably about 1000 Angstroms. The size of the pores is critical because the pores must be large enough to receive and retard the elution of the low molecular weight constituents during the first chromatographic separation to allow Factor VIII and the high molecular weight constituents to be eluted through the column rapidly and thus separated. Conversely, the pore cannot be of such a small diameter that the elution of dissociated Factor VIII is not held up as the high molecular weight constituents are rapidly eluted through the column during the second chromatographic separation and thus preventing separation of the dissociated Factor VIII from the high molecular weight constituents. The pore volume of the packing are from about 1.0 to about 1.8 ml per gram, especially preferred is a column packing with a pore volume of about 1.2 to about 1.5 ml per gram.

Packing of columns with small particle packing can be difficult because the particles must be packed next to each other to prevent the formation of channels. Channeling during chromatography will deleteriously effect separation. Preferably, the columns are slurry packed under high pressure, such as 2000 psi.

The aspect ratio of the column, that is the ratio of the depth of the packing to the internal diameter of the column, is preferably between about 10 and 40. Columns with low aspect ratios will give poorer separation, than columns with higher aspect ratios. The choice of a column aspect ratio will be dependent upon the degree of separation and time of separation desired.

The pressures employed in the separation step are not critical in themselves. Sufficient pressure is employed to elute the eluant at the desired rate. There is no lower limit to the amount of pressure that may be applied and pressures approaching atmospheric pressure may be used. Mechanical limitations of the equipment and the mechanical strength of the packing will limit the upper pressures that can be employed for the process. Pressures of 2500 psi or more can be employed, although the present process can be operated at pressures of from about 100 to about 2000 psi, preferably 200 to 1000 psi. The linear flowrate of the eluant through the column is normally dependent upon the degree of separation desired and the amount of time required for that degree of separation. For the first chromatographic separation of the present process, a linear flowrate of about 0.5 to about 10 cm per minute through the column has proven satisfactory and for the second chromatographic separation a linear flowrate of from about 1.2 to about 5.0 cm per minute through the column has been found satisfactory.

After the first chromatographic separation, the total volume of the fractions containing the Factor VIII is considerably more voluminous than the aqueous composition used as a feed for the first separation. Although not required, preferably the collected fractions, or second aqueous composition, are concentrated by conventional means, such as dialysis, lyophilization and the like. Preferably, the second aqueous composition is concentrated 5 to 10 fold to form the third aqueous composition having a protein concentration up to the solubility limits of Factor VIII and the high molecular weight constituents in the third aqueous composition, preferably from about 0.1 to about 200 g of protein per liter of composition, most preferably about 100 g of protein per liter. The Factor VIII after the first chromatographic separation is treated with a water soluble, physiologically compatible salt, such as sodium chloride, potassium nitrate, calcium chloride, preferably calcium chloride, at a sufficient concentration to dissociate the Factor VIII into its lower molecular weight forms. Any soluble physiologically compatible salt may be employed that will not deleteriously effect Factor VIII, Factor VIII:C, the column packing or the process itself. Conveniently and preferably, calcium chloride is used for the dissociation. When the salt concentration of the aqueous composition containing the Factor VIII:C is adjusted to about 0.2M or more, preferably from about 0.25 to about 0.5M, most preferably from about 0.3 to about 0.35M, Factor VIII dissociates into its lower molecular weight form having a molecular weight between about 0.9 and $3.0 \times 10^5$.

The composition containing the dissociated Factor VIII is applied to a chromatographic column which is preferably identical to or substantially similar to the first chromatographic column. The buffered aqueous eluant employed in the second chromatographic separation is substantially similar to the buffered aqueous eluant employed in the first chromatographic separation, except that the second eluant has a water soluable, physiologically compatible salt concentration of from about 0.25 to about 0.5M, preferably froma bout 0.3 to about 0.35M. The linear flowrate of eluant through the second column is preferably less than the linear flowrate of the eluant through the first column to enhance separation of dissociated Factor VIII from the high molecular weight constituents. In the second purification process, the dissociated Factor VIII is small enough to pass into the pores of the packing column thus retarding the elution of the dissociated Factor VIII. The high molecular weight constituents are too large to pass into the pores and are quickly eluted from the column thus achieving the desired separation.

The eluant from the chromatographic columns passes through a detector sensitive to proteinaceous material. The proteinaceous material of Factor VIII strongly absorbs light at wavelengths at between 254nm and 320nm. The absorption characteristics at any wavelength between 254 nm and 320 nm with conventional spectrophotometers. The fractions containing Factor VIII are collected and consolidated. The combined fractions are concentrated by conventional techniques, such as dialysis, freeze drying the like. The Factor VIII:C collected from the second chromatographic separation, can be concentrated, reassociated or processed for commercial utilization or for further research, such as for characterization of human, bovine or porcine Factor VIII structure.

DETAILED DESCRIPTION OF THE DRAWINGS

Figure 1:
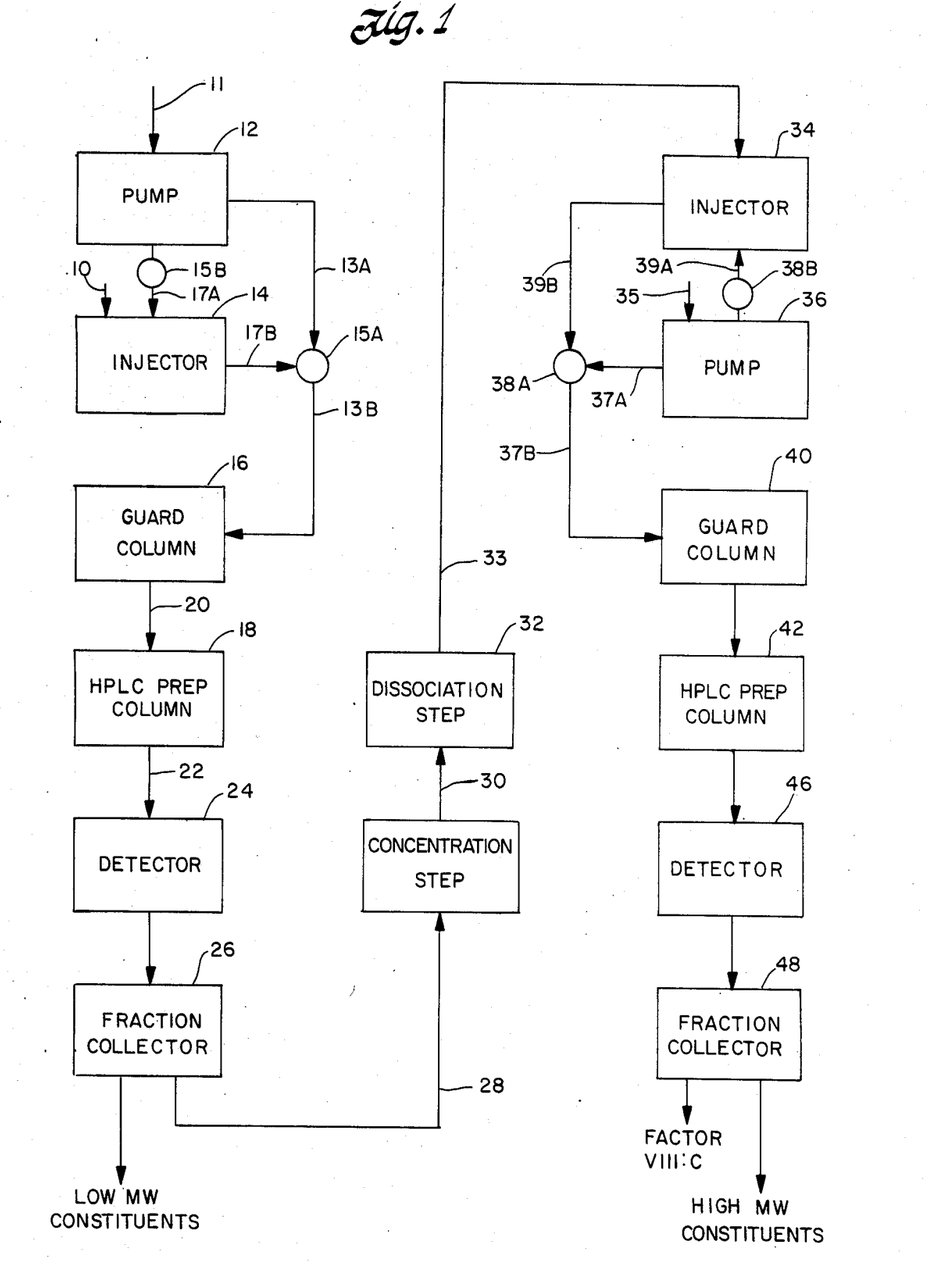
FIG. 1 is a flow diagram illustrating a preferred embodiment of the process of the present invention.

Referring first to FIG. 1, a buffered aqueous composition 10 of a plasma preparation comprising Factor VIII, high molecular weight constituents (impurities) and low molecular weight constituents (impurities) is introduced into injector 14. A buffered eluant 11 is introduced or siphoned into pump 12 and pumped into guard column 16 through line 13A, 3-way valve 15A and line 13B. The buffered composition 10 is pumped into guard column 16 by opening valve 15A to line 17B and closing valve 15A to line 13A and by opening valve 15B to pump eluant 11 from pump 12 through line 17A into injector 14 so as to inject composition 10 into guard column 16 through line 17B, valve 15A and line 13B. The eluant 11 and composition 10 are pumped at elevated pressures of from about 15 to about 3000 psi into and through guard column 16, HPLC prep column (high performance liquid chromatographic prepatory column) 18, detector 24 and fraction collector 26. The guard column 16 acts as a filter trap to collect material that would otherwise clog or plug the HPLC prep column 18. The filtered aqueous buffered composition flows under pressure from column 16 into the HPLC prep column 18 for the first chromatographic separation to separate the low molecular weight constituents from Factor VIII and high molecular weight constituents. The eluant 22 from the column 18 flows through a spectrophotometer detector 24, which is able to detect proteinaceous material, into a conventional fraction collector 26. The low MW (molecular weight) constituents, having a long distance of 100 nm or less, enter the pores of column packing and their elution is retarted. Factor VIII and the high molecular weight constituents are too large to enter the pores and are quickly eluted from the column thus separating them from the low molecular weight constituents. The fractions containing the low MW (molecular weight) constituents are discarded. The fractions containing Factor VIII and the high molecular weight constituents which are eluted before the low MW constituents are collected from fraction collector 26 and combined as stream 28. The combined fractions 28 are concentrated as described herein by conventional means to yield a concentrated buffered aqueous composition 30 which is treated with calcium chloride as described herein in dissociation step 32 to dissociate the Factor VIII into its lower molecular weight forms.

The dissociated Factor VIII composition, containing high molecular weight constituents, is injected into injector 34 through line 33. A buffered eluant 35 containing calcium chloride in approximately the same concentration as the dissociate Factor VIII composition is siphoned or introduced into pump 36 and pumped into guard column 40 through line 37A and 37B via 3-way valve 38A. The dissociated Factor VIII composition is injected as a slug by opening valve 38A to line 39B and closing valve 38A to line 37A, and by opening valve 38B to pump eluant 35 from pump 36 into injector 34 through line 39A and valve 38B, and from the injector 34, through line 39B, valve 38A and line 37B, into guard column 40. The injector contains a length of relatively small diameter tubing (not shown) connected at one end to line 39A and the other end to line 39B, and an injector port (not shown) communicating with the tubing for filling the tubing by injection with the dissociated Factor VIII composition.

The guard column 40, similar to guard column 16, acts as a filter trap to remove constituents that could plug or obstruct the HPLC prep column 42. The HPLC prep column is substantially identical to column 18. The dissociated Factor VIII composition is subject to chromatographic separation in HPLC prep column 42 to separate the dissociated Factor VIII from the high molecular weight constituents. Factor VIII:C is a lower molecular weight form of Factor VIII which can pass into the pores of column packing and is eluted from column 42 after the high molecular weight constituents which are too large to pass into the pores at column packing. Column 42 is eluted with the buffered eluant which is pumped into column 42 from pump 36 either through line 39A, valve 38B, injector 34, line 39B, valve 38A and line 37B, or through line 37A, valve 38A and line 37B. The eluant from column 42 is passed through a spectrophotometer detector 46, which is able to detect proteinaceous material, into fraction collector 48. The fractions containing Factor VIII:C are collected, combined and treated to further processing steps, such as processing into a a commercial Factor VIII:C concentrate for medicinal usage or for research purposes. The other fractions, including the fractions containing the high MW (molecular weight) constituents can be used for research purposes or otherwise disposed of. The guard column is a short column having particles of the same composition as the HPLC prep column of approximately the same particle size or larger. Little if any separation takes place in the guard column. The guard column's function is to trap out constituents that would plug the interstitial spaces between the particles of the HPLC prep column.

The following are examples of embodiments of the present invention. The following examples illustrate, but are not intended to restrict, the invention. It will be understood that the invention is not limited to the specific examples or the details recited therein.

EXAMPLE 1

Apparatus and Materials

The liquid chromatograph utilized in the following examples consists of a Model 6000A pump, a type UK6 injector containing a 10 ml sample loop, and a Model 450 variable wavelength detector, all products of Water Associates, Milford, Md. A semi-preparative TSK 5000 PW column (2.5×60 cm, particle size 17 microns) was used as a separation column and a TSK 6000 PW column (2.5×7.5 cm) was used as a guard column. These columns are distributed by Toyo Soda Manufacturing Co., Japan. Buffered aqueous solutions were made with HPLC grade water obtained from J. T. Baker, Phillipsburg, N.J. All chemicals utilized in the examples were reagent or analytical grade. Human 125-I-VIII:C was prepared as described by J. L. Moake et al, BLOOD, 61 (1983) 1163.

Protein Determination

Protein concentration was measured either by fluorometric assay described by P. Bohlen et al, ARCH. BIOCHEM. BIOPHYS., 155 (1973) 213 or by the method of M. Bradford, ANALYTICAL BIOCHEM., 72 (1976) 248 using bovine serum albumin (Fraction V, Sigma Chemical Co.) as a standard.

Coagulation Assays

Factor VIII:C activity for complex Factor VIII and dissociated Factor VIII was measured either by a two-stage thromboplastin generation test (TGT) time procedure described by L. Tocanthis et al, BLOOD COAGULATION IN HEMORRAGE AND THROMBOSIS, METHODS OF STUDY, New York, Grune & Stratton, 1965, or by a one-stage activated thromboplastin time test procedure as described by L. Tocantis et al, Supra, and E. J. W. Bowie et al, MAYO CLINIC LABORATORY MANUAL OF HEMOSTASIS, Philadelphia, W. B. Saunders, 1971, pg. 111. In both procedures severe hemophilia A plasma either obtained directly from patients or purchased from George King Biomedical, Inc., was used as a substrate. All Factor VIII:C assys were performed against a Factor VIII concentrate house standard calibrated against the Standard For Blood Coagulation Factor VIII Human (80/556) obtained from the National Institute for Biological Standards and Control, London, England. Duplicate Dissolutions at 1/100, 1/200, 1/400, and 1/800 were tested for each sample (except for column fractions) and the standard. In some cases Factor VIII:C activity in column fractions was determined colorimetrically using the KabiVitrum COATEST Assay Kit. This test determines Factor VIII:C activity based on its ability to convert Factor X to Factor $X_a$ and was found to yield results identical to those obtained using coagulation assays.

Purification of Factor VIII:C

Up to 10 bottles of commercial Factor VIII (complexed with von Willibrand Factor) concentrate (PROFILATE Brand Factor VIII Concentrate manufactured by Alpha Therapeutic Corporation, Los Angeles) were each rconstituted in three milliliters of water and pooled. Buffer exchange of the pooled material was performed by application of the pool sample to a Sephadex G-25 column (Pharmacia) and eluted with Buffer A (aqueous buffer: 50 mM imidazole.HCL, 150 mM NaCl, ph 7.0, 0.02% sodium azide). All detectable protein (as measured by absorbents at 280 nm) eluted in the void volume fractions were subsequently pooled. Up to 20 ml of the Factor VIII concentrate filtered on the Sephadex G-25 column were injected into a preparative Toyo Soda TSK 5000 PW column (2.5×60 cm) connected to a TSK 6000 PW guard column (2.5×7.5 cm) and eluted with Buffer A at a flowrate of 8.5 ml (per minute) equivalent to a linear elution rate of about 8 cm per minute through the column. Separate fractions were collected at 30 sec. intervals and analyzed for absorbance at 254 nm in a Gilford Model 2600 Spectrophotometer. Aliquots from each fraction were assayed for Factor VIII:C activity. Fractions were procoagulant activity were pooled and concentrated by dialysis against solid Aquacide II (Behring—Calbiochem). The concentrated protein sample was then made 0.35M in $CaCl_2$ by adding 1/9th volume of a 3.5M $CaCl_2$ solution to Buffer A to dissociate the complexed Factor VIII into its lower molecular weight forms. This material was then reinjected on the same HPLC column described above and eluted with Buffer A having a $CaCl_2$ concentration of 0.35M at a flowrate of 4.5 ml per minute (equivalent to a linear elution flowrate of about 3 cm per minute through the column). Separate fractions were collected at one minute intervals in silanized glassware. The eluant was analyzed continuously for absorbance at 280 nm. Aliquots from each fraction were diluted at least 8-fold prior to be assayed for Factor VIII:C activity. Active fractions were pooled and concentrated by a vacuum dialysis against Buffer A or Buffer A containing 25% by volume glycerol.

Chromatographic Separations

Approximately 1.5 gms of commercial Factor VIII (complexed with von Willibrand factor) concentrate (2 viles of Profilate Brand Factor VIII concentrate, Alpha Therapeutic Corporation) was filtered through a Sephadex G-25 Porous Column. The filtered Factor VIII concentrate was compounded into a buffered solution and injected into a Toyo Soda TSK 5000 PW column (2.5×60 cm) connected to a Toyo Soda TSK 6000 PW guard column (2.5×7.5 cm) and eluted with Buffer A at a flowrate of 8.5 ml per minute) equivalent to the linear flowrate through the column of about 8 cm per minute. Individual fractions were collected at one minute intervals and the absorbance of each fraction was determined spectrophotometrically at 254 nm. An aliquot from each fraction eluting after the void volume was diluted 400 fold and the length of time in seconds required for clot formation in the TGT assay that this dissolution was determined. Activity for each fraction is represented as 1/clotting time since clotting time for this assay is linearly related to Factor VIII:C activity in an inverse manner. Arrows at the top of FIG. 2 indicate positions at which standards of the indicated molecular weights are eluted from the columns under identical conditions. Standards injected were thyroglobulin, ferritin, bovine serum albumin, B-lactoglobulin and guanosine.

Figure 2:
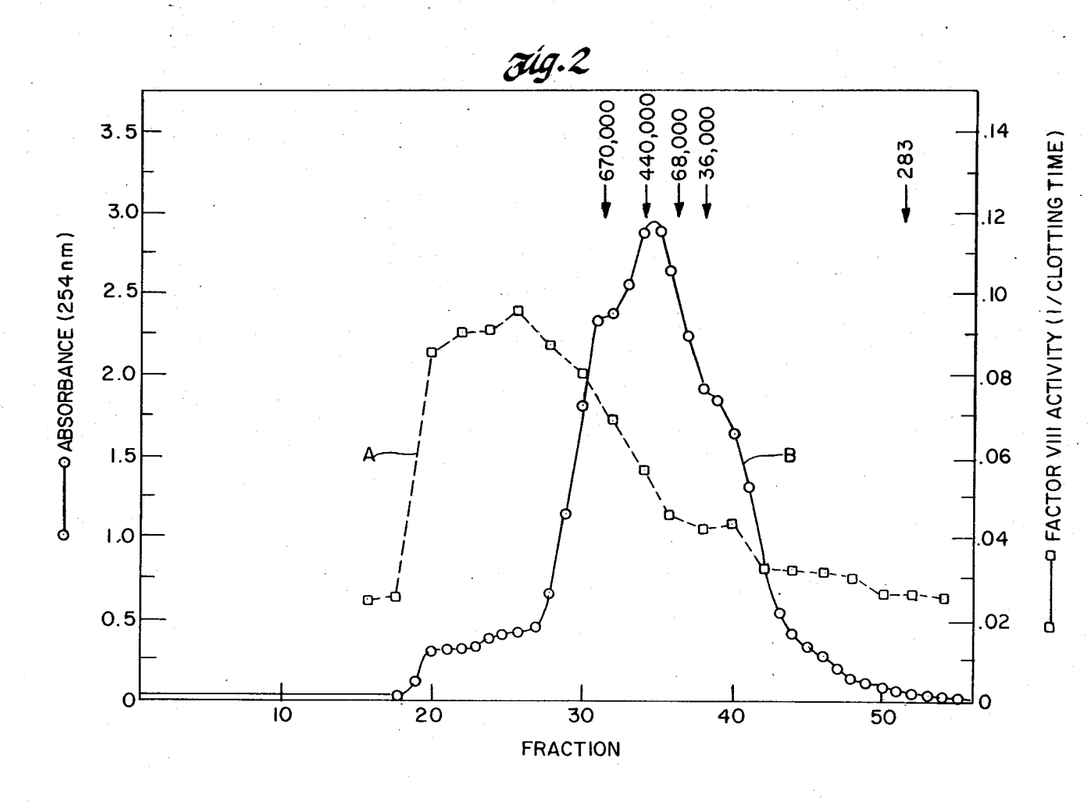
FIG. 2 is a graph showing the optical absorption curve at 254 nm (Graph A) and Factor VIII:C activity (Graph B) of the eluant resulting from passing a human plasma preparation through the first chromatographic column according to the process of the present invention.

As shown in FIG. 2, Factor VIII was separated from low molecular weight constituents present in the commercial Factor VIII preparations by high performance size exclusion chromatography on the semipreparative Toyo Soda TSK 5000 PW column in a low ionic strength buffer. In a low ionic strength buffer, Factor VIII:C is known to be associated with von Willibrand factor and its multimers as a high molecular weight complex. Factor VIII was found to be eluted from the column in the void volume at a molecular weight in excess of $2\times 10^6$ (see Graph A of FIG. 2). The entire separation took less than 25 minutes and up to 90% of the Factor VIII:C activity applied to the column could be recovered in a pool of active fractions which were eluted. The purification for this step was 20–40 fold. The isolated Factor VIII was thrombin activatable.

It was observed that as much as a 45% decrease in activity occurred upon subsequent concentration of the pool by either polyethylene glycol (4000) precipitation or dialysis against solid aquacide II. It is believed that most of this loss of Factor VIII:C activity results from the proteolytic attack of Factor VIII by the proteases in the impurities remaining with Factor VIII after the purification step. The concentration step is conducted at room temperature (about 21° C.); the proteases are active at this temperature.

Up to 4 gms of commercial Factor VIII concentrate could be chromatographed on the column at one time. However, because of the size of the sample loop for the chromatographic column, a total volume of only 10 ml could be injected at any one time, so that the actual amount of protein sample applied to the column was limited by the sample concentration and sample loop size. In some cases, several successive injections were required to purify the desired amount of material.

Filtration of the Factor VIII concentrate prior to purification by the present process is recommended. Less than 10% of the Factor VIII:C activity of the Factor VIII concentrate was lost after filtration on a Sephadex G-25 column.

Complexed Factor VIII:C (Factor VIII) can be dissociated from von Willebrand factor in the presence of high concentrations of $CaCl_2$. Approximately 20 mg of the Factor VIII purified in the above example was concentrated and compounded into a composition having a concentration of 0.35M $CaCl_2$ to dissociate the Factor VIII. The composition was chromatographed on the same high performance size exclusion liquid chromatography column as described in the above example. The column was eluted with Buffer A having a $CaCl_2$ concentration of 0.3M at a rate of 3 ml per minute (equivalent to a linear flowrate through the column of about 3 cm per minute). Individual fractions were collected at one minute intervals and the absorption of each fraction was determined spectrophotometrically at 280 nm with a Waters Model 450 spectrophotometer. All fractions eluted after the void volume was eluted were diluted 20 fold in a buffer containing 0.02% by weight sodium azide and having a imidazole HCl concentration of 0.05M and a pH of 7.0. These buffered compositions were assayed for factor VIII:C activity as described in the above example. Arrows at the top of FIG. 3 indicate positions at which molecular weight standard of the indicated molecular weight are eluted from the columns under identical conditions. The standards were the same as those used in the previous example. No dissociation of oligomeric protein molecular weight markers were observed.

Figure 3:
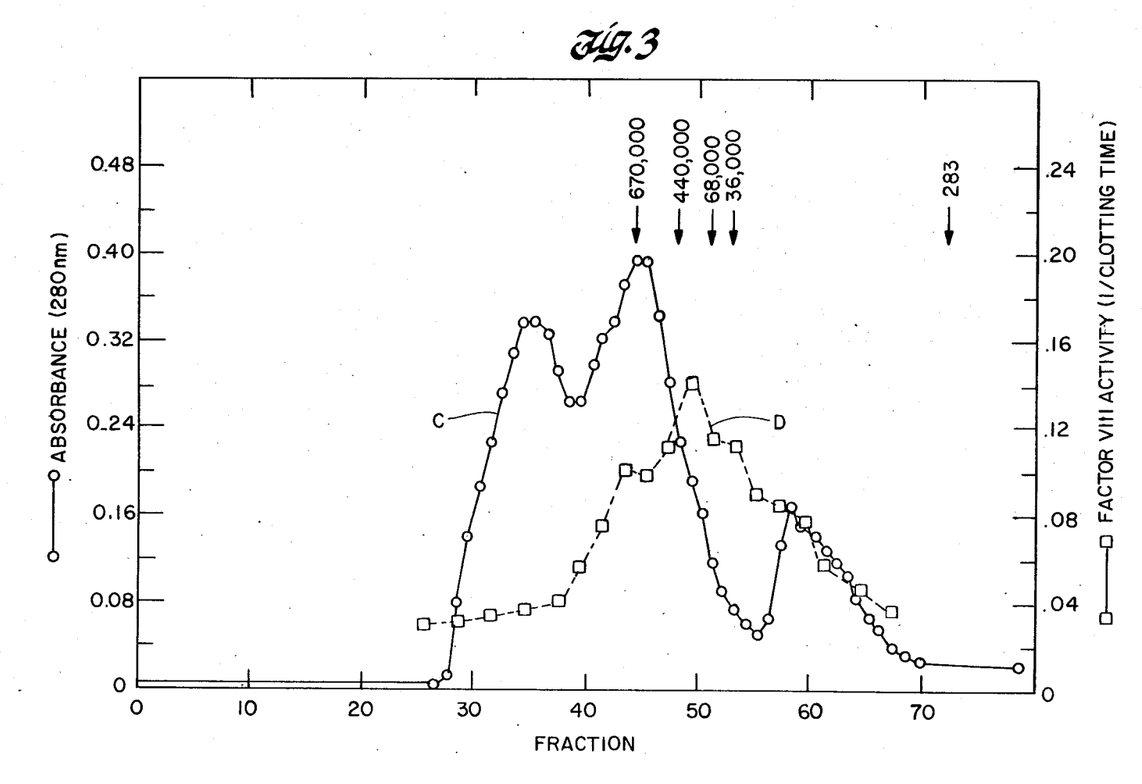
FIG. 3 is a graph showing the optical absorption curve at 280 nm (Graph C) and the Factor VIII:C activity (Graph D) of the eluant resulting from passing a human plasma preparation through the first and second chromatographic columns according to the process of the present invention.

Factor VIII:C activity was not eluted in the void volume but was eluted as a broad peak with a much lower apparent molecular weight indicating that the factor had been dissociated from the higher molecular weight complex (see Graph D of FIG. 3). The peak of factor VIII:C activity corresponds from approximate molecular weight of between 100,000 and 300,000 and is probably composed of the $2.6 \times 10^5$ molecular weight form of the molecule which was identified by 125-I-Fab-SDS polyacrylamide gel electrophoresis (as described below) and some of its cleavage products. When this method was used to further purify Factor VIII:C from the high molecular weight material isolated by high performance size exclusion liquid chromatography under a low ionic strength condition, a two to three fold increase in purity was generally observed. A 35% recovery of input activity was observed.

The high molecular weight complex containing Factor VIII:C (Factor VIII) will not flow through high performance liquid chromatography columns packed with particles of diameters of 10 microns or less.

The advantage of the present process lie in its speed of purification, its simplicity and its amenability to scale up for large commercial operations. The present process will be of tremendous value to the plasma fractionation industry and for the treatment of hemophilia A patients.

Gel Electorphoretic Analysis

Factor VIII:C was analyzed by gel electrophoresis analysis essentially as described by J. L. Moake Supra. Twenty-five microliters of the partially purified Factor VIII:C was incubated with 27 microliters of 125-I-Factor VIII:C Fab (13,000 total cpm) containing 5 mM diisopropylfluorophosphate (Aldrich), 95NIH U/ml irudin, 367 kallikrein inhibitor U/ml aprotinin (Trasylol, FBA Pharmaceuticals, New York, N.Y., and 3.2% by volume polyethylene glycol (average molecular weight 4000). Incubation was for 90 minutes at 37° C. and then for 30 minutes at 0° C. The reaction mixture was then warmed to room temperature and 52 microliters of a solution containing 0.18M Tris-HCL (pH 6.8), 6% (W/V) sodium dodecyl sulfate (SDS), 15% (W/V) 2-mercaptoethanol, and 30% (V/V glycerol) were added followed by incubation at 37° C. with gentle agitation. After 30 minutes the entire mixture was analyzed by electrophoresis on 5% polyacrylamide slab gels containing 0.1% SDS according to the procedure of U. K. Laemmli, NATURE (London), 227 (1970) 680. Protein molecular weight markers were electorphoresed in lanes of the slab gel adjacent to the lane containing the reaction mixture. After electrophoresis, the portion of the gel slab containing the molecular weight markers was removed and stained with a solution containing 25% (V/V) isopropanol, 10% (V/V) glacial acetic acid, and 0.15% (W/V) Coomassie Blue for two hours and then destained in 5% (V/V) methanol, 10% (V/V) glacial acidic acid. The relative mobility of individual markers in the gel was determined. The portion of the slab gel containing the reaction mixture sample was fixed in 25% (V/V) isopropanol, 10% (V/V) glacial acetic acid for two hours, then soaked in a solution containing 70% (V/V) ethanol, 10% (V/V) glacial acetic acid, and 5% (V/V) glycerol for 45 minutes, dried and placed with XAR-5 X Omat Film (Eastman Kodak, Rochester, N.Y.) and Kodak X-Omatic regular intensifying screens for five to seven days at −70° C. The relative mobilities of bands visible in the autoradiograph were determined and compared to those of the protein molecular weight markers.

Characterization of Molecular Weight Forms of Factor VIII:C

To determine the molecular weight forms of procoagulant complexed and dissociated Factor VIII present in the high performance size exclusion liquid chromatographic preparation, this material was incubated with human 125-I-VIII:C Fab and analyzed by SDS-5% polyacrylamide gel electrophoresis and audioradiography. The largest and most predominant band, the Factor VIII:C Ag+ 125-I-VIII:C Fab complex band, is a broad band with upper and lower molecular weight limits of $3.4 \times 10^5$ and $2.7 \times 10^5$ respectfully. These calculated as upper and lower molecular weight limits of $2.9 \times 10^5$ and $2.2 \times 10^5$ after subtracting the $0.5 \times 10^5$ molecular weight of the 125-I-VIII:C Fab. This molecular weight of approximately $2.6 \times 10^5$ is similar to the molecular weights reported by P. J. Faye et al and M. J. Weinstein as the molecular weight of intact procoagulant Factor VIII:C. This is the molecular weight form of Factor VIII:C that predominates ion fresh human plasma; this molecular weight form diminishes after activation of the Factor VIII:C molecule by proteolytic cleavage. A lower molecular weight form of Factor VIII:C is also evident in the audioradiogram and it has a calculated molecular weight of $1.1 \times 10^5$. The molecular form of Factor VIII:C with this molecular weight was reported by M. J. Weinstein et al, Supra, and it is believed to be derived from the $2.6 \times 10^5$ molecular weight form by protolytic cleavage. Additional forms of Factor VIII:C with the molecular weights of less than $2.6 \times 10^5$ are known to exist but were not observed in the audioradiogram suggesting that they were not present in the high molecular weight complex isolated by high performance size exclusion liquid chromatography.

What is claimed is:

1. A process for isolating Factor VIII procoagulant protein (Factor VIII) from a plasma preparation comprising Factor VIII, high molecular weight constituents and low molecular weight constituents by high performance size exclusion chromatography comprising the steps of:
   (a) preparing a buffered aqueous composition of a plasma preparation comprising Factor VIII, the high molecular weight constituents and the low molecular weight constituents;
   (b) separating the low molecular weight constituents from said buffered aqueous composition by introducing said composition on a chromatographic column of porous high performance liquid chromatography beads having a particle size of from about 13 to about 35 microns, the particles having pores with diameters of from 500 to about 2000 angstroms and a pore volume of from about 1.0 to about 1.8 ml per gram, eluting the chromatographic column with a buffered aqueous eluant, and selecting those fractions of the eluant immerging from the column containing the Factor-VIII and high molecular weight constituents substantially free of the low molecular weight constituents to obtain a second aqueous composition.

2. The process according to claim 1 wherein the buffered aqueous composition comprises a soluble, physiologically compatible inorganic chloride salt having a concentration of from about 0.07 to about 0.3M, and imidazole.HCL in a concentration of from about 0.025 to about 0.075M, and the buffered aqueous eluant comprises a soluble, physiologically compatible inorganic chloride salt having a concentration of from about 0.07 to about 0.3M and imidazole.HCL in a concentration of from about 0.025 to about 0.075M, the buffered aqueous composition and the buffered aqueous eluant, independently, having a pH of from about 5.5 to about 8.0.

3. The process according to claim 2 wherein said buffered aqueous composition and said buffered aqueous eluant each have a soluble, physiologically compatible inorganic chloride salt concentration of about 0.15M and a imidazole.HCL concentration of about 0.05M; said buffered aqueous composition and said buffered aqueous eluant each having a pH of 7.0.

4. The process according to claim 1 wherein said high molecular weight constituents have a molecular weight at least equal to the molecular weight of Factor VIII, and said lower molecular weight constituents have a molecular weight no greater than about $1.0 \times 10^6$.

5. The process according to claim 1 wherein the buffered aqueous composition is eluted through the chromatographic column at a linear rate of about 0.5 to about 10 cm per minute.

6. The process according to claim 1 wherein the ratio of the length of the packing of the beads in the chromatographic column to the internal diameter of the chromatographic column is from about 10 to about 40.

7. The process according to claim 1 wherein said buffered aqueous composition is eluted through the chromatographic column under pressure of from about 100 to about 2000 psi.

8. The process according to claim 1 wherein said buffered aqueous composition is eluted through the chromatographic column under pressure of from about 200 to about 1000 psi.

9. The process according to claim 1 including the additional steps of:
   (c) dissociating the Factor VIII in said second aqueous composition into its lower molecular weight forms by adjusting the soluble salt concentration of said second aqueous composition above about 0.2M to produce a third aqueous composition containing dissociated Factor VIII and the higher molecular weight constituents; and
   (d) separating the higher molecular weight constituents from dissociated Factor VIII in said third aqueous composition by introducing said composition on a chromatographic column of porous high performance liquid chromatography beads having a particle size of from about 13 to about 35 microns, the particles having pores with diameters of from about 500 to about 2000 angstroms and a pore volume of from about 1.0 to about 1.8 ml per gram, eluting the chromatographic column with a second buffered aqueous eluant having a soluble salt concentration above about 0.2M, and selecting the fractions of eluant immerging from the column containing dissociated Factor VIII substantially free of said higher molecular weight constituents.

10. The process according to claim 9 wherein said third aqueous composition and said second buffered aqueous eluant contain a soluble, physiologically compatible inorganic chloride salt having a concentration of from about 0.07 to about 0.3M and imidazole.HCL having a concentration of from about 0.025 to about 0.075M; said third aqueous composition and said second buffered aqueous eluant each, independently, having a pH of from about 5.5 to about 8.0.

11. The process according to claim 10 wherein said third aqueous composition and said second buffered aqueous eluant have a soluble, physiologically compatible inorganic chloride salt concentration of about 0.15M and an imidazole.HCL concentration of about 0.05M; each of said third aqueous composition and said second buffered aqueous eluant having a pH of about 7.0.

12. The process according to claim 9 wherein the high molecular weight constituents have a molecular weight at least equal to the molecular weight of Factor VIII.

13. The process according to claim 9 wherein the third aqueous composition is eluted through the chromatographic column at a linear rate of from about 1.2 to about 5.0 cm per minute.

14. The process according to claim 9 wherein the length of the packing of the porous beads in the chromatographic column of step (d) to the internal diameter of the chromatographic column of step (d) is from about 10 to 40.

15. The process according to claim 9 wherein the third aqueous composition is eluted through the chromatographic column of step (d) under pressure of from about 100 to about 2000 psi.

16. The process according to claim 9 wherein the third aqueous composition is eluted through the chromatographic column of step (d) under pressure of from about 200 to about 1000 psi.

17. The process according to claim 1 wherein the porous high performance liquid chromatography beads in the chromatographic column have a particle size of from about 15 to about 19 microns, and pores with an average diameter of about 1000 angstroms.

18. The process according to claim 9 wherein the porous high performance liquid chromatography beads in the chromatographic column have a particle size of from about 15 to about 19 microns and pores with an average diameter of about 1000 angstroms.

19. A process for isolating Factor VIII procoagulant protein (Factor VIII) from a plasma preparation comprising Factor VIII, high molecular weight constituents having a molecular weight at least equal to Factor VIII and low molecular weight constituents having a molecular weight no greater than $1.0 \times 10^6$ by high performance size exclusion chromatography comprising the steps of:

(a) preparing a buffered aqueous composition of a plasma preparation comprising Factor VIII, high molecular weight constituents having a molecular weight at least equal to the molecular weight of Factor VIII and low molecular weight constituents having a molecular weight no greater than $1.0 \times 10^6$, said composition having a soluble, physiologically compatible inorganic chloride salt at a concentration of from about 0.07 to about 0.3M, imidazole.HCL at a concentration of from about 0.025 to about 0.075M, and a pH of from about 5.5 to about 8.0;

(b) separating the low molecular weight constituents from said buffered aqueous composition by introducing said composition on a chromatographic column of porous high performance liquid chromatography beads having a particle size of from about 13 to about 35 microns, the particles having pores with diameters of from about 500 to about 2000 Angstroms and a pore volume of from about 1.0 to about 1.8 ml per gm, eluting the chromatographic column with a buffered aqueous eluant having a soluble physiologically compatible inorganic chloride concentration of about 0.07 to about 0.3M, imidazole.HCL at a concentration of from about 0.025 to about 0.075M, and a pH of from about 5.5 to about 8.0, and selecting and collecting those fractions of the eluant immerging from the column containing Factor VIII and high molecular weight constituents substantially free of the low molecular weight constituents to obtain a second aqueous composition;

(c) concentrating said second aqueous composition to obtain a third aqueous composition containing Factor VIII and high molecular weight constituents, said third composition having a protein concentration of about 20 to about 200 g of protein per liter of composition;

(d) dissociating the Factor VIII into its lower molecular weight forms in said third aqueous composition by adding a soluble, physiologically compatible salt to said third aqueous composition to adjust the salt concentration to from about 0.25 to about 0.5M to produce a fourth aqueous composition; and (e) separating the high molecular weight constituent having a molecular weight at least equal to the molecular weight of Factor VIII from said fourth aqueous composition by introducing said composition on a chromatographic column of porous high performance liquid chromatography beads having a particle size of from about 13 to about 35 microns, the particles having pores with diameters of from about 500 to about 2000 Angstroms and a pore volume of from about 1.0 to about 1.8 ml per gm, eluting the chromatographic column with a buffered aqueous eluant having a soluble physiologically compatible inorganic chloride salt concentration of about 0.07 to about 0.3M, a soluble, physiologically compatible salt concentration of from about 0.25 to about 0.45M and a pH of from about 5.5 to about 8.0, and selecting the fractions of the eluant immerging from the column containing dissociated Factor VIII substantially free of said high molecular weight constituents.

20. The process according to claim 19 wherein the buffered aqueous composition, the buffered aqueous eluant, the fourth aqueous composition and the second buffered aqueous eluant contain a soluble, physiologically compatible inorganic chloride salt at a concentration of about 0.15M and imidazole.HCL in a concentration of about 0.05M; each of said aqueous buffered compositions, first buffered aqueous eluant, said fourth aqueous composition and said second buffered aqueous eluant having a pH of about 7.0.

21. The process according to claim 19 wherein the ratio of the length of the porous beads in said chromatographic columns and the internal diameter of said columns is from about 10 to about 40.

22. The process according to claim 19 wherein said first aqueous composition is eluted through the first chromatographic column at a linear rate of about 0.5 to about 10 cm per minute; said fourth aqueous composition is eluted through the chromatographic column at a linear rate of about 1.2 to about 5.0 cm per minute.

23. The process according to claim 22 wherein said buffered aqueous composition is eluted through the chromatographic column at a pressure between about 100 and about 2000 psi and said fourth aqueous composition is eluted through the chromatographic column at a pressure of about 100 to about 2000 psi.

24. The process according to claim 22 wherein said buffered aqueous composition is eluted through the chromatographic column at a pressure between about 200 and about 1000 psi and the fourth aqueous composition is eluted through the chromatographic column at a pressure of about 200 to about 1000 psi.

25. The process according to claim 18 wherein the porous high performance liquid chromatography beads in the chromatographic columns have particle sizes of from about 15 to about 17 microns, and pores with average diameters of about 1000 angstroms.

* * * * *

UNITED STATES PATENT AND TRADEMARK OFFICE
CERTIFICATE OF CORRECTION

PATENT NO. : 4,675,385

DATED : June 23, 1987

INVENTOR(S) : Steven W. Herring

It is certified that error appears in the above-identified patent and that said Letters Patent is hereby corrected as shown below:

Column 1, line 16, "Willibrand" should read --Willebrand--; column 1, line 18, "Willibrand" should read -- Willebrand --; column 1, line 35, "hemophiliac" should read -- hemophilia --; column 1, line 62, before "plasma" insert -- blood --; column 2, line 18, "auxilliary" should read -- auxiliary --; column 2, line 50, before "ammonium", "a" should read -- an --; column 2, line 52, before "CL-4B" delete the "("; column 2, line 67, "inventioon" should read -- invention --; column 3, line 25, "enhance" should read -- enhanced --; column 3, line 35, "constitutes" should read -- constituents--; column 4, line 23, "Preferrably" should read -- preferably --; column 4, line 27, "preferrably" should read -- preferably --; column 4, line 49, "factor" should read -- Factor --; column 4, line 56, "deminsions" should read -- dimensions --; column 5, line 29, after ";" insert -- and --; column 5, line 35, after "invention" delete "; and" and insert therefor --.--; column 5, line 43, after "low" and before "performance" insert -- molecular weight constituents (impurities) by high--; column 5, line 51, "5.55" should read -- 5.5 --; column 5, line 60, "ml/bm" should read -- ml/gm --; column 6, line 19, after "salt to" delete "of"; column 6, line 24, after "Factor" "III" should read -- VIII --; column 6, line 47, "hyophilized" should read -- lyophilized --; column 7, line 36, before "from" delete "are" and insert therefor -- is --; column 8, line 35, "3.0X105" should read -- $3.0 \times 10^5$ --; column 8, line 43, "soluable" should read -- soluble --; column 8, line 45, "froma bout" should read -- from about --; column 8

UNITED STATES PATENT AND TRADEMARK OFFICE
CERTIFICATE OF CORRECTION

PATENT NO.  : 4,675,385

DATED       : June 23, 1987

INVENTOR(S) : Steven W. Herring

It is certified that error appears in the above-identified patent and that said Letters Patent is hereby corrected as shown below:

line 61, after "characteristics" and before "at" insert -- of the fractions eluted from the columns may be monitored--; column 8, line 66, after "drying" insert -- and --; column 9, line 23, "prepatory" should read -- preparatory --; column 9, line 37, "retarted" should read -- retarded --; column 10, line 25, after "into a" delete "a" (second occurrence); column 11, line 17, "assys" should read -- assays --; column 11, line 42, "ph" should read -- pH--; column 11, line 55, after "Fractions" delete "were" and insert therefor -- with --; column 12, line 10, "viles" should read --vials--; column 13, line 62, "Electorphoretic" should read -- Electrophoretic --; column 14, lines 15,16, "electorphoresed" should read -- electrophoresed --; column 14, line 48, "respectfully" should read -- respectively --; column 14, line 56, "ion" should read -- in --; column 16, line 55, before "40" insert -- about --.

Signed and Sealed this

Ninth Day of August, 1988

Attest:

DONALD J. QUIGG

Attesting Officer

Commissioner of Patents and Trademarks